US011285093B2

(12) United States Patent
Bezivin

(10) Patent No.: US 11,285,093 B2
(45) Date of Patent: Mar. 29, 2022

(54) COSMETIC USES OF SWERTIAMARIN

(71) Applicant: LUCAS MEYER COSMETICS, Paris la Defense (FR)

(72) Inventor: Carine Bezivin, Verrieres le Buisson (FR)

(73) Assignee: International Flavors & Fragrances Inc., Union Beach, NJ (US)

( * ) Notice: Subject to any disclaimer, the term of this patent is extended or adjusted under 35 U.S.C. 154(b) by 0 days.

(21) Appl. No.: 15/124,717

(22) PCT Filed: Mar. 9, 2015

(86) PCT No.: PCT/FR2015/050569
§ 371 (c)(1),
(2) Date: Sep. 9, 2016

(87) PCT Pub. No.: WO2015/136198
PCT Pub. Date: Sep. 17, 2015

(65) Prior Publication Data
US 2017/0020796 A1 Jan. 26, 2017

(30) Foreign Application Priority Data
Mar. 10, 2014 (FR) ...................................... 1451920

(51) Int. Cl.
| | |
|---|---|
| *A61K 8/60* | (2006.01) |
| *A61Q 19/08* | (2006.01) |
| *A61K 36/51* | (2006.01) |
| *A61Q 19/00* | (2006.01) |
| *A61K 8/9789* | (2017.01) |
| *A61K 8/73* | (2006.01) |
| *A61K 9/00* | (2006.01) |
| *A61K 9/16* | (2006.01) |
| *A61K 31/7048* | (2006.01) |

(52) U.S. Cl.
CPC ................ *A61K 8/602* (2013.01); *A61K 8/73* (2013.01); *A61K 8/9789* (2017.08); *A61K 9/0014* (2013.01); *A61K 9/1652* (2013.01); *A61K 31/7048* (2013.01); *A61K 36/51* (2013.01); *A61Q 19/007* (2013.01); *A61Q 19/08* (2013.01); *A61K 2800/74* (2013.01)

(58) Field of Classification Search
None
See application file for complete search history.

(56) References Cited

U.S. PATENT DOCUMENTS

| | | | | |
|---|---|---|---|---|
| 6,692,754 B1 * | 2/2004 | Makimoto | ........... | A61K 8/4913 424/401 |
| 2002/0009472 A1 * | 1/2002 | Takekoshi | ................ | A61K 8/65 424/401 |
| 2008/0194620 A1 * | 8/2008 | Besne | .................. | A61K 8/4926 514/307 |

FOREIGN PATENT DOCUMENTS

| | | | |
|---|---|---|---|
| CN | 1966511 | * | 5/2007 |
| EP | 1 023 889 | | 8/2000 |
| FR | 2811226 | * | 1/2002 |
| JP | 6422811 | * | 1/1989 |
| JP | 07145033 | * | 6/1995 |
| JP | 2005-002056 | | 1/2005 |
| JP | 2008-001602 | | 1/2008 |
| JP | 2009263262 | * | 11/2009 |
| KR | 2011-0072997 | | 6/2011 |

OTHER PUBLICATIONS

Helfrich et al. Overview of Skin Aging and Photoaging. Dermatology Nursing vol. 20, No. 3. pp. 177-183 (Jun. 2008).*
Roginson and Aasi. Cosmetic concerns and management strategies to combat aging. Maturiatas vol. 70. pp. 256-260 (2011).*
Jang English Machine Translation of KR 2011-0072997 [online]. KIPO [retrieved on May 23, 2017]. Retrieved from the internet: <http://kposd.kipo.go.kr:8088/up/kpion/>.*
Xiaobing English Translation Abstract Only of CN 1966511 [online]. Espacenet [retrieved on May 23, 2017], Retrieved from the internet: <http://www.epo.org/searching-for-patents/technical/espacenet.html#tab1>.*
English Human Translation of KR2011-0072997 (Jang). Phoenix Translations, May 2017, pp. 1-26.*
Machine Translation of FR 2811226 (Courtin) [online]. Espacenet [retrieved on Oct. 30, 2017]. Retrieved from the internet: <www.espacenet.com>.*
Machine Translation of Ichiro JP 07145033 [online]. Original document published: Jun. 6, 1995 [retrieved on Oct. 10, 2018], Retrieved from the internet: <http://dossier.ipdl.inpit.go.jp/text_trans.html>. (Year: 1995).*
Human Translation of Ichiro JP 07145033; publication date Jun. 6, 1994; Translated by LinguaLinx Language Solutions, Inc; received by the USPTO on Oct. 24, 2018. (Year: 2018).*
Nobuaki English Machine Translation [online], Espacenet 2009 [retrieved on Sep. 21, 2019], Retrived from the internet: <www.epo.org>. (Year: 2009).*
Seiberg. "Non-denatured Soyean Extracts in Skin Care: Multiple Anti-aging Effects," Soybean=Biochemistry, Chemistry and Physiology, Prof. Tzi-Bun Gn (ed.); pp. 119-136. (Year: 2011).*
Human Translation of Miyamoto JP 64022811; publication year 1989. Translated by Schreiber Translation, Inc. Provided to the Office Nov. 2019. (Year: 2019).*

(Continued)

Primary Examiner — Katherine Peebles

(57) ABSTRACT

The present invention relates to the uses of swertiamarin or of a plant extract enriched with swertiamarin, for stimulating the formation or regeneration of the epidermis and/or for stimulating the metabolism of the dermis mainly in the cosmetics field.

14 Claims, 4 Drawing Sheets

(56) References Cited

OTHER PUBLICATIONS

Kimura et al. Fitoterapia vol. 82, pp. 827-833. (Year: 2011).*
Database GNPD [online] Accession No. 2298297, "Sleeping Mask" Jan. 2014, XP-002732077, pp. 1-3.
Database GNPD [online] Accession No. 2281373, "Lalima Blood and Skin Purifier" Jan. 2014, XP-002732078, pp. 1-4.
Written Opinion in International Application No. PCT/FR2015/050569, dated May 28, 2015, pp. 1-5.
Seiberg, M. "Non-denatured Soybean Extracts in Skin Care: Multiple Anti-Aging Effects" Chapter 8 from *Soybean—Biochemistry, Chemistry and Physiology*, Prof. Tzi-Bun Ng (Ed.), Apr. 26, 2011, pp. 119-136.
Phoboo, S. et al. "Quantification of Major Phytochemicals of *Swertia chirayita*, a Medicinal Plant From Nepal" *EcoPrint*, 2010, pp. 59-68, vol. 17.

* cited by examiner

COSMETIC USES OF SWERTIAMARIN

CROSS-REFERENCE TO RELATED APPLICATION

This application is the U.S. national stage application of International Patent Application No. PCT/FR2015/050569, filed Mar. 9, 2015.

FIELD OF THE INVENTION

The present invention relates to the cosmetic field, in particular to cosmetic agents capable of stimulating the formation or the regeneration of skin.

BACKGROUND OF THE INVENTION

The skin is the first barrier protecting the body from outer aggressions. This organ is formed of several tissue layers. Distinction can be made between the epidermis, which is the outermost portion of the skin, the dermis, a connective tissue consisting of fibroblasts and an extracellular matrix, which ensures the functions of cohesion and nutrition of the skin, and the hypodermis consisting of adipocytes.

The epidermis is formed of several keratinocyte cell strata. Inter alia, a distinction is made between the germinative layer of the epidermis, called the basal layer, notably containing the cutaneous stem cells, the spinous layer, Stratum spinosum, consisting of several layers of polygonal cells, the granulous layer, Stratum granulosum, comprising one to three layers of flattened cells containing cytoplasma inclusions, keratohyalin grains and finally the corneal layer, Stratum corneum which consists of anucleated and keratin-enriched cells called corneocytes which correspond to the terminal stage of differentiation of keratinocytes.

The outermost cells of the corneal layer are continuously removed and replaced by the cells from a lower layer, according to a process called desquamation. Cell regeneration of the corneal layer is based on a cell maturation process in which the cells of the basal layer of the epidermis differentiate and gradually migrate through the different strata of the epidermis until they reach the corneal layer in the form of corneocytes.

Skin ageing, whether it results from a normal senescence phenomenon or whether it is enhanced by an external factor such as exposure to UV radiations, implies dysfunctions of the differentiation and/or of cell renewal resulting in an atrophy of the whole skin foundations.

From a histological point of view, a decrease in the quality of the dermis is inter alia observed, in particular a loss of consistency of the extracellular matrix, and a decrease in the thickness of the epidermis.

From an aesthetic point of view, these alterations results in a modification of the aspect of the skin and of its mechanical properties: the skin is less smooth, or even rough and may become dehydrated or even dry. Its micro-relief is more pronounced, and may have fine lines, which may lead over time to the formation of deep wrinkles. The skin may also exhibit a loss of elasticity and of firmness, and a less bright complexion.

The skin may exhibit other alterations of its visual aspect, in particular stretch marks or red spots.

Many cosmetic products intended to prevent or attenuate wrinkles or attenuate red spots or stretch marks are present on the market.

However, at the present time, a need remains for new active ingredients for preventing or treating skin alterations, especially those resulting from skin ageing.

SUMMARY OF THE INVENTION

A first object according to the invention is the cosmetic use of swertiamarin or that of a swertiamarin-enriched plant extract in order to stimulate the formation or the regeneration of the epidermis and/or to stimulate the metabolism of the dermis. Said swertiamarin or said plant extract may be used as an anti-ageing agent, an anti-wrinkle agent, a skin complexation unifying agent, an anti-redness agent or for a skin smoothing agent.

The plant extract enriched with swertiamarin is preferably an extract obtained from a species of *Swertia*, such as *Swertia chirata* or *Swertia milensis*, and which comprises at least 90% by weight of swertiamarin. For this purpose, the swertiamarin or the plant extract is present, as an active agent, in a composition, preferably a cosmetic composition, intended to be administered via a topical route.

Said composition is preferably intended to prevent or treat a sign of skin ageing or stretch marks. It may also be intended for making subcutaneous micro-vessels less visible. Said composition may also be intended for preventing, treating or attenuating a skin redness.

The signs of skin ageing encompass a thinning of the skin, in particular of the epidermis, the occurrence of micro-relief, the occurrence of fine lines and/or wrinkles on the skin, included at the lips and at the eyelids, shrinkage or collapse of the skin, a loss of radiance of the skin, periorbital dark circles, a dull complexion, a loss of skin density, a loss of skin firmness, a loss of skin tonicity, a loss of skin elasticity, an alteration of the smooth aspect of the skin, and/or an increase in the roughness of the skin. In certain embodiments, the composition is intended to treat or prevent a transient or permanent redness, preferably in a skin type selected from the group consisting of a skin with a tendency to be affected by couperosis, a skin with a tendency to be affected by erythrosis and a skin with a tendency to be affected by erythrosis and couperosis.

Swertiamarin generally represents from 0.0001% to 10% by weight, preferably between 0.001% and 5% by weight, more preferably between 0.005% and 0.5% by weight of the total weight of said composition.

In certain embodiments, said composition further comprises, at least one additional cosmetic agent, preferably selected from the group consisting of vitamins, sun filters and sunscreens, anti-ageing agents, or anti-wrinkle agents, antioxidants, lifting agents, firming agents, anti-spot agents, anti-redness agents, slimming agents, draining agents, moisturizing agents, soothing agents, scrubbing or exfoliating agents, mattifying agents, sebum regulating agents, skin lightening actives, self-tanning actives, tanning accelerators and combinations thereof.

In other embodiments, said composition may be in various forms. It may be selected from the group consisting of aqueous solutions, hydro-alcoholic solutions, oil-in-water emulsions (O/W) or water-in-oil emulsions (W/O) or multiple emulsions (triple: W/O/W or O/W/O), nanoemulsions, in particular O/W nanoemulsions, for which the size of the drops is less than 100 nm, aqueous gels, or dispersions of a fatty phase in an aqueous phase by means of spherules, suspensions, preferably in an aqueous or hydroalcoholic media, suspensions of liposomes, powders, lotions, milks, creams, ointments, gels, foams, and pomades.

In particular embodiments, the composition appears as a cosmetic product, a makeup product or a body hygiene product, for example a lotion, a milk, a serum, an aqueous or oily gel, an emulsion, a cream, a cream-gel, a skin care water, a pomade, a balm, a foundation, a spray, an eye shadow, a stick, a lipstick, a gloss, a lip balm, a foam, a deodorizer, a nutritive face mask, a shower gel, and an exfoliating or scrubbing product. An object of the present invention is also the use of swertiamarin or that of a plant extract enriched with swertiamarin as a healing agent or as an epidermis regenerating agent, in the treatment or prevention of a lesion of the skin or of a mucosa, in particular a cut, cracks, wounds or micro-wounds, chapped skin, a split, or craze lines.

Said swertiamarin or said extract are preferably intended to be administered topically and, optionally, in combination with another active ingredient, preferably selected from the group consisting of soothing agents, moisturizers, anti-inflammatory agents, antioxidant agents, healing agents, disinfecting agents, antimicrobial agents (including antibiotics and antifungal agents) and combinations thereof.

An additional object according to the invention is the use of a pharmaceutical or cosmetic composition in the treatment of a lesion of the skin or of a mucosa, said composition comprising swertiamarin or a plant extract enriched with swertiamarin as a healing agent or an agent for regenerating the epidermis. Said composition may comprise from 0.0001% to 10% by weight, preferably between 0.001% to 5% by weight, more preferably between 0.005% and 0.5% by weight of swertiamarin. Said composition may further comprise an additional active ingredient preferably selected from the group consisting of soothing agents, moisturizers, anti-inflammatory agents, antioxidant agents, healing agents, disinfecting agents, antimicrobial agents and combinations thereof.

The plant extract enriched with swertiamarin may be an extract obtained from a species of *Swertia*, preferably *Swertia chirata* or *Swertia milensis*, and which comprises at least 90% by weight of swertiamarin.

Finally, an object of the invention is also a composition for preparing a pharmaceutical or cosmetic composition, comprising:
- from 0.1 to 20% of swertiamarin, said swertiamarin being preferably integrated in the form of a plant extract enriched with swertiamarin, in particular an extract obtained from a species of *Swertia* such as *Swertia chirata* or *Swertia milensis*,
- from 50% to 99.9% of a carrier, preferably selected from a filler, an aqueous solvent, an organic solvent, preferably a lower alcohol such as ethanol, propanediol, butylene glycol, glycerol or isopropanol, a lipophilic agent and mixtures thereof, and
- optionally, from 0.1 to 30% of an additional excipient pharmaceutically or cosmetically acceptable, preferably selected from a vectorization agent, an antioxidant agent, a preservative, a stabilizer, a thickener, an emulsifier, a hydrophilic or lipophilic gelling agent, a perfume, a mineral or organic oil, and combinations thereof, the percentages being expressed by weight based on the total weight of the composition.

This so called "precursor" composition is preferably selected from:
- a solid composition appearing in the form of a powder in which swertiamarin is absorbed on a filler, for example maltodextrin, and
- a composition appearing in the form of water-in-oil emulsion comprising a lipophilic agent, preferably selected from fatty acids, fatty acid esters such as isopropyl palmitate and/or fatty alcohols and an emulsifier or vectorization agent selected from phospholipids, hydrogenated derivatives thereof and mixtures thereof.

PRESENTATION OF THE FIGURES

Figure 5:
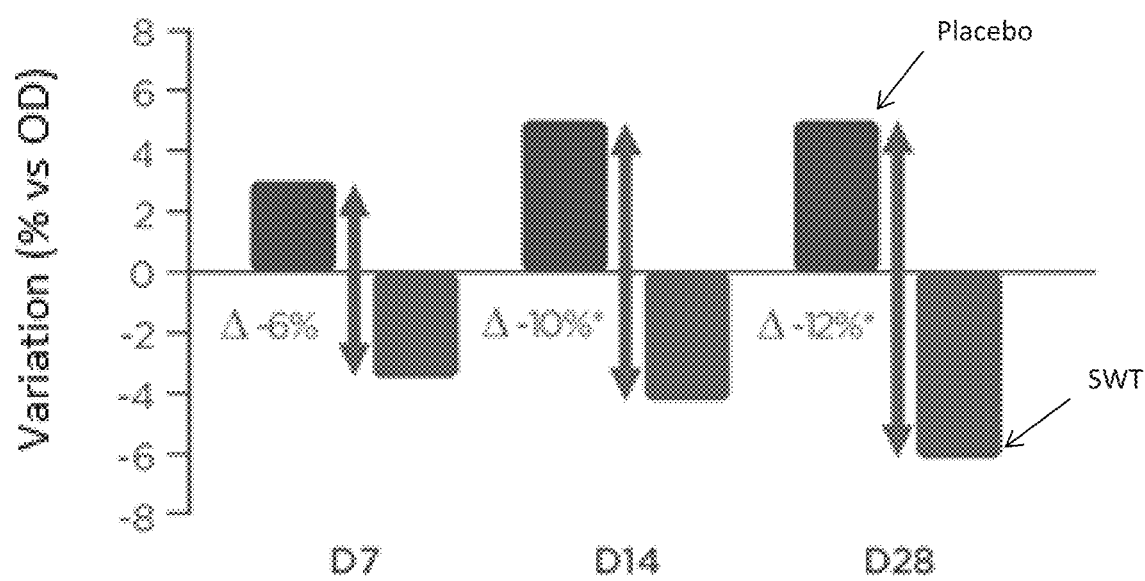

FIG. 5 is a graph showing the variation percentage of the wrinkle volume relative to the reference value measured at D=0, for skins treated with the placebo cream (Placebo) and the skins treated with the "SWT" cream (SWT). An increase in the volume of the wrinkles is observed for skins treated with the placebo cream. On the other hand, twice daily application of the "SWT" cream allows to decrease the volume of the wrinkles over time, illustrating the anti-wrinkle effect of swertiamarin (see Example 6—clinical test no. 2).

Figure 6:
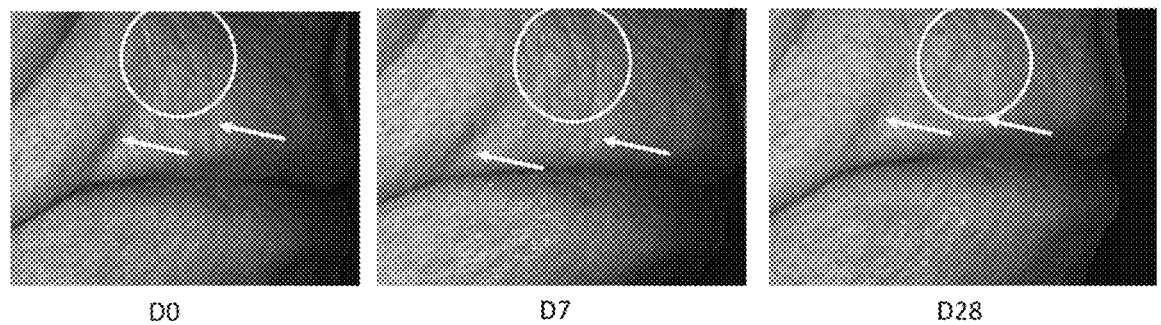

FIG. 6 shows macrophotographs of the contour of the lips of a 64 year old volunteer at D=0 (D0), D=7 (D7) and D=28 (D28) of the treatment with the SWT cream. A clear reduction of the relief of the wrinkles is observed at the upper contour of the lip on the macrophotographs from D7 and D28. The skin appears smoother (see Example 6—clinical test no. 3).

Figure 7:
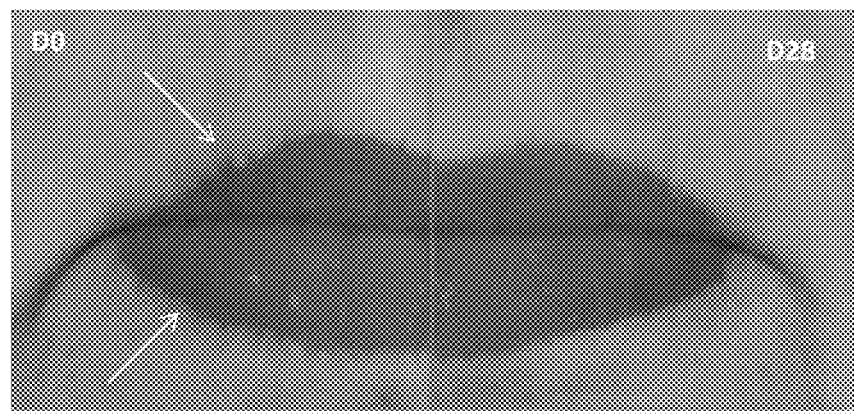

FIG. 7 shows the photograph of the contour of the lips of a volunteer 50 years of age at D=0 (D0) and at D=28 (D28) of the treatment with the SWT cream. The migration of the lipstick is significantly greater at D=0 (D0) than at D=28 (D28) (see Example 6—clinical test no. 4).

DESCRIPTION OF THE INVENTION

The genus *Swertia* belongs to the family of Gentianacea and group about 150 plant species, mainly in Asia and in Africa. *Swertia* species are used in several traditional medicines. As an example, the species *Swertia chirata* (also known under the name of *Swertia chirayita*) is an indigenous species of the Himalaya used in Ayurveda, notably for its hypoglycemic, antipyretic, antiparasitic, and antibacterial properties as well as for its tonifying properties on the digestive system.

In traditional medicine, the entire plant is generally used for preparing powders which are administered as an infusion, as a decoction or as a tincture. Studies have shown that the plants of the *Swertia* genus comprise a very large number of compounds of the xanthonoid, alkaloid, terpenoid, flavonoid, and iridoid type potentially having biological activity (Brahmachari et al., CHEMISTRY & BIODIVERSITY Vol. 1 (2004), 1627-1651). Swertiamarin (CAS No.: 17388-39-5) is one of the many compounds which was isolated from *Swertia* species, notably *Swertia Chirata* and *Swertia milensis*. This compound was also isolated from other plants of the Gentianacea family, for example certain species of the *Gentiana* and *Centaurium* genus. The chemical formula of swertiamarin is as follows:

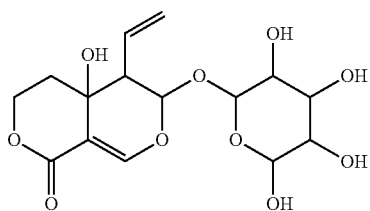 [SMILES: C=CC1C(OC2OC(O)C(O)C(O)C2O)OC=C2C(=O)OCCC21O]

Swertiamarin is marketed in a purified form (purity of at least 95%) or as enriched extracts.

Swertiamarin was described in the scientific literature, inter alia, for its antidiabetic, anti-gastric, analgesic, antimicrobial and anti-cholesterol properties.

The present invention relates to novel uses of swertiamarin, or of plant extracts enriched with swertiamarin, in the cosmetic and therapeutic field.

Surprisingly, the Applicant showed that swertiamarin was capable of stimulating the proliferation of keratinocytes. In particular, the Applicant demonstrated that swertiamarin induces production of the keratinocyte growth factor (KGF) by adipocyte cells (Example 1). The Applicant also showed on the basis of a test of the "Scratch assay" type that it was possible to induce the proliferation of keratinocytes by incubating them in the presence of a culture of adipocytes pretreated with swertiamarin (Example 2). Swertiamarin was also capable of promoting the growth of human skin explants and of increasing the thickness of the epidermis (Example 3). Finally, the Applicant demonstrated that swertiamarin was capable of directly stimulating the metabolism of the dermis, in particular stimulating the production of fibronectin, a key glycoprotein of the extracellular matrix (Example 4). Because of its capability of inducing the proliferation of keratinocytes and/or the production of constitutive glycoproteins of the dermis, swertiamarin finds direct application in cosmetics, in particular as an anti-wrinkle or anti-ageing agent for preventing or treating signs of skin ageing. The Applicant thus showed that daily application of a cream having a content of about 0.024% by weight of swertiamarin gave the possibility of significantly attenuating the wrinkles and decreasing the roughness of the skin, in particular in the region of nasolabial folds and of the contour of the lips (see Example 6). More generally, swertiamarin may be used as a cosmetic for treating or preventing non-pathological alteration of the skin requiring restoration or regeneration of the epidermal tissue. As an example, swertiamarin may be used as an anti-redness agent. Swertiamarin also finds applications in the therapeutic field, especially as a healing agent or as an epidermis regenerating agent, for example in the treatment or the prevention of skin or mucosa lesions.

Uses of Swertiamarin According to the Invention

In the context of the present document, swertiamarin may be used as an isolated product or as a plant extract enriched with swertiamarin. The swertiamarin-enriched plant extract may be obtained from a plant belonging to the family of Gentianacea, such as species of the genus *Swertia*. *Gentiana* or *Centaurium*. Preferably, the plant extract enriched with swertiamarin is obtained from a plant or a portion of a plant (leaf, flower, stem and/or seed) belonging to the genus *Swertia* such as *Swertia Chirata* or *Swertia milensis*. By "an extract enriched with swertiamarin" is meant an extract comprising at least 90% by weight of swertiamarin. It is obvious that an extract enriched with swertiamarin according to the invention does not encompass a powder directly obtained by milling of the entire plant of *Swertia* or of one of its parts.

In certain embodiments, swertiamarin is used as a plant extract of *Swertia* comprising at least 80%, preferably at least 90% by weight of swertiamarin. In certain embodiments, this is an extract of *Swertia Chirata* or of *Swertia milensis*. A plant extract comprising at least 90% by weight of swertiamarin encompasses a plant extract comprising (or having a content) of at least 91%, 92%, 93%, 94%, 95%, 96%, 97%, 98%, 99% or even 99.5% by weight of swertiamarin, said percentage being based on the total weight of the extract. In certain embodiments, the plant extract enriched with swertiamarin according to the invention comprises at least 80%, preferably at least 90% by weight of swertiamarin and at most 20%, preferably at most 10% by weight of compounds other than swertiamarin, in particular impurities. The impurities or the other compounds present in the extract according to the invention may either stem from the initial plant matrix, or from one of several chemical compounds used during the extraction process.

The preparation of such extracts is described in the state of the art. Several extracts adapted to the application of the present invention are commercially available. These extracts may be obtained from any portion of a plant known as containing swertiamarin, such as seeds, leaves, roots, stems or further flowers. In certain preferred embodiments, the extract enriched with swertiamarin is obtained by an extraction process from leaves of a species of *Swertia*, in particular *Swertia Chirata*. The process may comprise a percolation step or an extraction step with an organic solvent, especially an alcohol such as ethanol. It may further comprise one or several additional steps aiming at increasing the swertiamarin content, for example one or several steps selected from concentration, precipitation, filtration or chromatography steps.

According to a first aspect, an object of the present invention is uses, preferably cosmetic and non-therapeutic, of swertiamarin. Swertiamarin may be used, preferably for cosmetic purposes, for stimulating the formation or the regeneration of the epidermis, in particular stimulating the proliferation of keratinocytes. In certain particular embodiments, swertiamarin, or an swertiamarin-enriched plant extract, such as an extract of *Swertia chirata*, may be used for cosmetic purposes, as an agent for stimulating the proliferation of keratinocytes, as an agent for increasing or restoring the thickness of the epidermis, or further as an agent stimulating the formation or the regeneration of the epidermis.

By "restoring the thickness of the epidermis" is meant the fact of increasing the thickness of the epidermis, i.e. increasing the number of keratinocyte layers of the epidermis so as to obtain an epidermis thickness equivalent to the one observed for the epidermis of young skin. Swertiamarin may also be used for stimulating the production of a skin protein. By "skin protein" is meant any constitutive protein of the extracellular matrix, in particular collagen and fibronectin.

According to an additional aspect, swertiamarin may be used for cosmetic purposes for stimulating the metabolism of the dermis, in particular for stimulating the production of fibronectin in the dermis.

An object of the present invention is also the cosmetic use of swertiamarin for promoting regeneration and/or restoration of the dermis and/or of the epidermis, or further for controlling or preventing non-pathological atrophy of the epidermis.

In particular, swertiamarin may be used for preventing or treating a non-pathological alteration of the skin. By "non-pathological alteration of the skin" is meant any non-pathological modification of the visual aspect or of the mechanical properties of the skin. Non-pathological alterations of the skin may in particular result from skin ageing, from fragility or sensitivity of the skin (a so called reactive skin) or from the exposure of the skin to certain outdoor conditions.

In certain embodiments, swertiamarin may therefore be used as an anti-ageing or anti-wrinkle cosmetic.

In the sense of the invention, the term of "skin" refers to any portion of the skin of the human body, in particular the skin of the face, including the lips and the eyelids, the neck, the skin of the hands and the skin of the feet.

By "skin ageing signs" is in the sense of the invention meant any alteration or modification of the visual aspect or of the mechanical properties of the skin, in particular of the epidermis, non-pathological, resulting from skin ageing, whether it is chronological (chrono-ageing) and/or photo-induced (photo-ageing).

Thus, the signs of ageing encompass, without being limited thereto, a thinning of the skin, in particular of the epidermis, the occurrence of a micro-relief, the occurrence of fine lines and/or wrinkles on the skin, including at the lips and at the eyelids, wilting or collapse of the skin, loss of radiance of the skin, a dull complexion, circles at the eyes, a loss of density of the skin, a loss of firmness of the skin, a loss of tonicity of the skin, a loss of elasticity of the skin, an alteration of the smooth aspect of the skin, and/or an increase in the roughness of the skin.

As examples, because of its properties on the proliferation of keratinocytes and/or on the metabolism of the dermis, swertiamarin may be used in a cosmetic context for:
- stimulating the metabolism of the epidermis and/or regenerating the epidermis, in particular for controlling ageing of the skin, more particularly of the epidermis;
- improving the radiance of the complexion or unifying the complexion;
- limiting pigmentary spots,
- preventing, attenuating or treating eye circles,
- rejuvenating ageing skin,
- preventing, attenuating or treating the wrinkles, and/or the fine lines, in particular in mature skins;
- smoothing the skin, or limiting its roughness;
- correcting the refining of the skin related to age;
- preventing or treating the dryness of the skin, preferably by increasing the barrier effect of the epidermis,
- maintaining or improving the mechanical characteristics of the skin, such as tonicity, firmness, flexibility and/or elasticity of the skin, and/or
- smoothing and/or restructuring the lips, and/or for making them softer, less rough with a better defined contour.

Within the scope of the present invention, by "preventing a sign of skin ageing" is meant the fact of preventing, slowing down or delaying the occurrence of the sign of skin ageing. By "treating a sign of skin ageing" is meant the fact of correcting, attenuating, diminishing, making less visible, reducing the appearance or even making the sign of skin ageing disappear.

In certain embodiments, swertiamarin is used in a cosmetic way for preventing or treating a sign of skin ageing, preferably selected from a thinning of the epidermis, the occurrence of a microrelief, the occurrence of fine lines and/or wrinkles on the skin, including at the lips and at the eyelids, a loss of radiance of the skin and an alteration of a mechanical property of the skin such as a loss of density, of firmness, of flexibility and/or elasticity.

In this respect, swertiamarin is particularly effective for preventing or treating wrinkles and fine lines of the face, in particular the vertical wrinkles of the face, for example located around the lips or at the bottom of the face in the region of the nasolabial folds.

By "smoothing the skin" is meant the fact of attenuating and/or correcting the relief of the skin, including the lips, said relief appearing as a wrinkle, fine lines and/or stretch marks, and may even be consecutive to the presence of varicose veins. Preferably, the relief of the skin appears as wrinkles, fine lines and/or roughness of the skin.

The effect on the sign of skin ageing or the smoothing effect of the skin may be evaluated by one of the methods described in Example 6, in particular by means of a facial imaging system Visia-CR®, or an imaging system by projecting fringes such as the Primos® 3D Pico system by comparing a treated skin area with a composition comprising swertiamarin or an extract enriched with swertiamarin versus a skin area treated with a placebo cream. Swertiamarin may also be used, as a cosmetic, for preventing or treating other non-pathological alteration types of the skin implying a non-pathological dysfunction of the renewal of the epidermis. It may be the case, for example, for stretch marks or redness. Stretch marks may be formed during the menopause, pregnancy or during a significant weight loss or gain. As an example, swertiamarin may be used as an anti-stretch mark agent, for example for reducing the appearance of stretch marks. Swertiamarin may also be used for making varicose veins less visible.

With skin ageing and exposure to outdoor conditions, the epidermis may become thinner and no longer perfectly play its role as a barrier. The skin then becomes more sensitive and subject to rednesses and to skin dryness. Moreover, the thinning of the skin may make the subcutaneous micro-vessels more visible, which may enhance the intensity of the red spots.

Thus, because of its capability of inducing the proliferation of keratinocytes, swertiamarin may also be used, preferably as a cosmetic and non-therapeutic agent, as an anti-redness agent. In the sense of the invention, an "anti-redness agent" encompasses:
- an agent capable of preventing, treating or attenuating red spots.
- an agent capable of reducing the tendency of blushing of a skin such as a reactive, fragile or sensitive skin, in particular in response to an external factor, or further
- an agent capable of attenuating the red aspect associated with surface micro-vessels or with an abnormality of the subcutaneous vascular system or making said abnormality less visible.

In the sense of the invention, "an abnormality of the subcutaneous vascular system" inter alia encompasses telangiectasia and angioma.

In the sense of the invention, the term of "redness" encompasses red spots and skin overheating, in particular at the face for example at the cheeks, the nose and the chin.

These may be red spots or sporadic, transient or temporary overheating (also called "flushes") which may be induced or promoted by an external factor, in particular by a weathering condition such as exposure to UVs, wind, a too low or too high room temperature or a sudden change in temperatures, by ingestion of a foodstuff, for example a hot drink, an alcohol or spices, or further by a stress or an emotion. These may also be settled or permanent rednesses, for example associated with the presence of surface micro-vessels, with an angioma or with a telangiectasia. Finally, these may be temporary or permanent redness associated with couperosis or erythrosis. Preferably, the term of "redness" refers to the red areas associated with the presence of surface micro-vessels, with couperosis or with erythrosis.

In certain embodiments, the redness is due to surface micro-vessels associated with couperosis or erythrosis. In other embodiments, the redness is due to surface micro-vessels which are not associated with couperosis or erythrosis.

In other embodiments, swertiamarin is used for treating or preventing the occurrence of transient or permanent redness in a skin type selected from a sensitive skin, a fragile skin, a reactive skin, an intolerant skin, a skin with a tendency to be affected with couperosis, a skin with a tendency of being affected with erythrosis or a skin with a tendency of being affected by erythrosis and couperosis.

By a skin with a tendency to be affected by erythrosis or couperosis is meant a skin which may be affected by couperosis or erythrosis.

Because of its general action on the rednesses, the spots and the eye circles, swertiamarin may also be used as a complexion unifying agent.

Swertiamarin may also be used for making less visible, at the surface of the skin, a varicose vein, surface micro-vessels, an angioma or a telangiectasia. The surface micro-vessels may be congenital, or consecutively appear upon skin ageing or development of couperosis. This action of swertiamarin is notably based on its capability of stimulating the dermis and the epidermis, more particularly on its capability of promoting the proliferation of keratinocytes and therefore restore or increase the thickness of the epidermis.

In cosmetic uses according to the invention, swertiamarin is present, as an active agent, in a composition, preferably a cosmetic composition.

Swertiamarin may be incorporated into the composition in a purified form or as a plant extract enriched with swertiamarin as previously defined. In certain embodiments, the swertiamarin is present as a plant extract comprising at least 90% by weight of swertiamarin, said plant extract being preferably an extract of *Swertia chirata* or *Swertia milensis*.

This composition is preferably intended to be administered topically. Typically, the composition is intended to be applied on the skin, for example on the skin of the hands or of the face, including the lips or the eyelids.

Swertiamarin (or the plant extract enriched with swertiamarin) is generally present in the composition in an amount comprised and ranging from 0.0001% to 10%, preferably between 0.001% to 5% by weight, more preferably between 0.001% and 0.5% or even from 0.005% to 0.1%, the percentages being expressed based on the total weight of the cosmetic composition. As an example, swertiamarin may be present in an amount from 0.01% to 0.1% by weight, for example in an amount from 0.015% to 0.040% by weight of the cosmetic composition. The composition may further comprise, one or several additional active ingredients. Preferably, the additional active ingredient(s) exert(s) a cosmetic effect. By "active ingredient with a cosmetic effect, active agent with a cosmetic effect, or active with a cosmetic effect" is meant a compound capable of exerting at least one cosmetic effect on the skin or its annexes. By "cosmetic effect" is meant any non-therapeutic effect aiming at modifying and/or improving the aspect of the skin or of the mucosas like lips, protecting them from external aggressions (sun, wind, humidity, dryness, chemical products), or further preventing and/or correcting phenomena related to their ageing.

Thus, in certain embodiments, swertiamarin may be present in a composition which further comprises an active ingredient with an additional cosmetic effect. This active ingredient with a cosmetic effect may be selected from the group consisting of vitamins, sun filters and sunscreens, anti-ageing or anti-wrinkle agents, anti-redness agents, antioxidants, lifting agents, firming agents, moisturizers, soothing agents, scrubbing or exfoliating agents, mattifying agents, sebum regulating agents, skin-lightening actives, anti-spot actives, slimming agents, draining agents, self-tanning actives, tanning accelerators and combinations thereof. In particular, the cosmetic composition may comprise tocopherols, and/or plant extracts like flax seed extracts, exopolysaccharide extracts from *Vibrio*, peptides like trifluoroacetyl tripeptide-2.

Preferably, the cosmetic composition may comprise an active selected from an anti-wrinkle agent, an anti-ageing agent, an anti-redness agent, an antioxidant agent, a moisturizer active, a soothing agent, a sebum regulating agent, an anti-spot agent and combinations thereof. Still more preferably, the active agent with an additional cosmetic effect is selected from an anti-wrinkle agent, an anti-ageing agent, an antioxidant agent, a moisturizer, a lifting agent, a firming agent and combinations thereof.

The additional active ingredient(s) with a cosmetic effect are typically present in an amount from 0.0001% to 10% by weight of the composition.

As an example of moisturizers, mention may be made of urea, pidolic acid (PCA) and derivatives thereof in particular its salts such as arginine PCA, chitosan PCA, copper salts (Copper PCA), magnesium salts (magnesium PCA), sodium salts (sodium PCA) or zinc salts, ethylhexyl PCA, calcium gluconate, hyaluronic acid and its salts and other glycosaminoglycans, fructose, glucose, isomaltose, lactose, trehalose, polydextrose, saccharose (Sucrose), maltitol, mannitol, sorbitol, xylitol and other carbohydrates and derivatives, polyethylene glycols such as PEG-7, PEG-8, PEG-10, PEG-12 or PEG-14, glycerol, propylene glycol, butylene glycol, betain, citrullin, collagen and its derivatives, histidine, silk, keratin or soya hydrolysates, plant extracts rich in polysaccharides and/or polyphenols, for example Aloes extracts, cornflower (*Centaurea cyanus*), and combinations thereof.

As an example of anti-ageing, anti-wrinkle agents or lifting agents, mention may be made of ascorbic acid and its derivatives such as magnesium ascorbyl phosphate, glycosaminoglycans and derivatives thereof, ribose, sorbitol, *Cyathea* polysaccharides, collagen, flax seed extracts (*Linum usitatissimum*), peptides such as caprooyl-tetrapeptide-3 and trifluoroacetyl tripeptide-2, extracts of *Polygonum aviculare*, brown algae extracts, in particular of *Ascophyllum nodosum*, fern extracts, in particular of *Cyathea Cumingii*. As example of soothing agents, mention may be made of allantoin, aloes, birch (for example *Betula alba*), epilobe (*Epilobium angustiblium*), chestnut (for example *Castenea sativa*), cornflower (for example *Centaurea cyanus*), centella (for example *Centella asiatica*), common horsetail (for example *Equisetum arvense*), fennel (for example *Foeniculum vulgare*), hamamelis (for example *Hamamelis virginana*), ivy (for example *Hedera helix*), *habiscus sabdariffa*, lilies (for example *Lilium candidum*), mallow (for example *Malva sylvestris*), melissa (for example *Melissa officinalis*), skullcap (for example *Scutellaria baicalensis*), mimosa (for example *Mimosa tenuiflora*), potentilla (for example *Potentilla erecta*) extract, an extract of oligosaccharides or one oligosaccharide, for example from flax, peptides like palmitoyl tripeptide-8, polysaccharides obtained by biotechnology like the extract of a ferment of *Alteromonas* and combinations thereof.

As an example of antioxidants, mention may be made of HMR (hydroxy methyl resorcinol), ascorbic acid and derivatives thereof, vitamin B9, histidine hydrochloride, or an extract of epilobe (*Epilobium augustifolium*). The active ingredients with an antioxidant effect and of the vitamin type are generally used in a mass percentage of at least 1% based on the total weight of the cosmetic composition.

As an example of sebum regulating agents, mention may be made of flax lignans, rice powder, zinc gluconate, sarcosine, an extract of *Cinnamomum zeylanicum* bark, an avocado extract and combinations thereof.

As anti-redness agents, mention may be made of saponins, flavonoids, ruscogenins, esculosides, and extracts containing them, for examples *Ruscus* extracts, as well as certain essential oils for example of lavender or rosemary.

As an example of anti-spot agents, mention may be made of extracts such as licorice (*Glycyrrhyza glabra*), jackfruit extract (*Artocarpus heterophyllus*), *Rumex* extract (*R. occidentalis*), plant extracts belonging to the citrus genus, extracts of plants rich in stilbenes like resveratrol, peptides like the oligopeptide-68, nonapetide-1, arbutin, kojic acid, magnesium ascorbyl phosphate and combinations thereof.

An object of the invention is also a cosmetic process for treating, attenuating or preventing a sign of skin ageing, a redness or a skin overheating in an individual, said process comprising the administration of a cosmetically effective amount of swertiamarin, preferably topically.

Another object according to the invention is a cosmetic process for smoothing the skin in an individual, for example for correcting or attenuating wrinkles, fine lines or stretch marks, said process comprising the administration of a cosmetically effective amount of swertiamarin, preferably topically.

Another object according to the invention is a cosmetic process for making less visible or improving the aspect of a varicose vein, of surface micro-vessels, of an angioma or a telangiectasia in an individual, said process comprising the administration of a cosmetically effective amount of swertiamarin, preferably topically, on the skin area where the varicose veins, the surface micro-vessels, the angioma or the telangiectasia is/are visible.

As indicated specifically, swertiamarin is typically administered as a composition, said composition preferably being a cosmetic composition applied on the skin, for example on the face, the neck or the hands.

According to an additional aspect, an object of the present invention is the use of swertiamarin in the field of healing lesions of the skin or of the mucosas. Thus, swertiamarin may be used for promoting healing, in particular for promoting regeneration of the epidermis, reconstruction of the epidermis and/or promoting re-epithelization of the skin or of mucosas affected by a lesion. Preferably this is a therapeutic use of swertiamarin. More generally, swertiamarin may be used for preventing or treating a lesion of the skin or of mucosas. Swertiamarin may thus be used for therapeutic purposes as a healing agent or an agent for re-epithelization or regeneration of the epidermis.

As mentioned herein before, swertiamarin may be used as an isolated product or as a plant extract enriched with swertiamarin, preferably obtained from a plant belonging to the *Swertia* genus such as *Swertia Chirata* or *Swertia milensis*.

The lesion may correspond to trauma of the skin or of the mucosa, for example a cut, a scratch, a burn, including a chemical, thermal or contact burn, an irritation, an erythema, or further a blister or a vesicle. The lesion may result from exposure of the skin or of a mucosa to weather aggressions, such as wind or strong variations of temperatures, to certain chemicals such as detergents, to certain therapeutic agents such as anti-cancer or anti-acne agents, to radiotherapy, to laser or further to certain cosmetic processes such as peeling or dermo-abrasion.

The lesion may also result from a pathology, in particular from a dermatosis such as pruritus, eczema, atopic dermatitis.

The lesion of the skin or of the mucosa may correspond to surface cracks or to deeper cracks such as chapped skin or split.

In certain embodiments, swertiamarin may be used for treating a lesion of the skin or of a mucosa such as a cut, a burn, an irritation, a vesicle, a blister, cracks, micro-wounds, a chapped skin, a split, or craze lines. Preferably, the lesion of the skin or of a mucosa is selected from a cut, cracks, a wound, micro-wounds, a vesicle, a crevasse, or cracking. As an example, these may be cracks or chaps at the lips or the hands or further cracking or crevasses at the heels.

In order to apply therapeutic uses according to the invention, swertiamarin (or the plant extract enriched with swertiamarin) may be incorporated into any type of composition, whether it is a cosmetic or pharmaceutical composition. Like in the case of cosmetic uses, the composition is preferably intended to be administered topically, for example to be applied on the skin or on the mucosa to be treated. Swertiamarin I generally present in the composition in an amount comprised, ranging from 0.0001% to 10%, preferably between 0.001% to 5% by weight, more preferably between 0.001% and 0.5% even from 0.005% to 0.1%, the percentages being expressed based on the total weight of the cosmetic or therapeutic composition. As an example, swertiamarin may be present in an amount from 0.01% to 0.1% by weight, for example in an amount of 0.015% to 0.040% by weight of the cosmetic or therapeutic composition.

The composition may further comprise one or several additional active ingredients selected from actives with a cosmetic effect and/or from among actives with a therapeutic effect. As an example, the additional active ingredient may be selected from the group consisting of soothing agents, moisturizers, anti-inflammatory agents, antioxidant agents, healing agents, agents promoting regeneration of the epidermis, disinfecting agents, antimicrobial agents for example anti-fungal agents, disinfecting agents or antibiotic agents and combinations thereof.

Typically, the soothing agents, the moisturizers, and the antioxidant agents listed earlier for their cosmetic uses according to the invention may also be used within the scope of uses in the field of healing according to the invention.

As an example of agents promoting regeneration of the epidermis, mention may be made of madecassol, oxaceprol, an extract from *Calendula officinalis*, an extract from *hypericum* (*Hypericum perforatum*), an extract from yarrow (*Achilea millefolium*), an extract of *Ledum palustre*, zinc oxide, Peru balsam, vitamin A (retinol), dexpanthenol.

As examples of anti-inflammatory agents, mention may be made of corticoids, salicylic acid and nonsteroidal anti-inflammatory agents.

As disinfecting agents, mention may be made of chlorhexidine, quaternary ammoniums; triclocarban, anionic derivatives, organic mercury compounds, copper or zinc salts, derivatives of para-hydroxybenzoic acid, hexamidine and derivatives thereof, iodineated derivatives.

As antibiotics, mention may be made of macrolids, fusidic acid, aminosids, rifamycin, sulfamides.

As antifungal agents, mention may be made of imidazole and derivatives thereof, terbinafin, selenium sulfide.

The additional active ingredient(s) are typically present in an amount from 0.0001% to 10% by weight of the composition.

According to another aspect, an object of the present invention is the use of swertiamarin in combination with an active agent preferably selected from soothing agents, moisturizers, anti-inflammatory agents, antioxidant agents, healing agents, antimicrobial agents including antifungal agents, disinfecting agents or antibiotics, in the treatment or prevention of a lesion of the skin or of a mucosa or for promoting healing. Swertiamarin and the additional active agent may be administered simultaneously, successively or separately over time.

According to an additional aspect, an object of the present invention is a method for treating or preventing a lesion of the skin or of a mucosa in a patient, said method comprising the administration to said patient of an effective amount of swertiamarin, preferably topically.

According to another aspect, an additional object according to the invention is the use of swertiamarin for preparing a composition, preferably a cosmetic or pharmaceutical composition, intended for treatment or prevention of a lesion of the skin or of a mucosa.

In the methods and uses according to the invention, the dose to be administered and the administration frequency of swertiamarin vary depending on the sought cosmetic effect or therapeutic effect, on the characteristics of the individual in particular the gender thereof, the age thereof and the skin type thereof. For the cosmetic uses according to the invention, the posology may vary according to the ageing sign(s) which one wishes to prevent or treat. For the therapeutic uses according to the invention, the posology may vary depending on the type and seriousness of the lesion which one wishes to treat.

Typically, within the scope of a cosmetic use according to the invention, swertiamarin may be applied, on the areas to be treated, once or twice daily, typically in the morning and/or the evening, for several consecutive weeks or even several months, for example at least for 1 month, for example at least for 3 months. Within the scope of a therapeutic use according to the invention, swertiamarin may be applied, on the wound to be treated in an amount from two to three times daily, preferably until complete healing, for example for a week.

As a particular example of cosmetic methods according to the invention, mention may be made of a method for preventing, attenuating or treating a skin ageing sign in an individual, said method comprising the application of a cosmetic composition comprising swertiamarin or a plant extract enriched with swertiamarin on the skin at least once a day, for at least seven days.

Preferably, the ageing sign is selected from thinning of the epidermis, a wrinkle or fine line, the occurrence of a microrelief, especially a roughness, and combinations thereof. The skin area to be treated is preferably selected from the hands, the neck, the face or a portion of the face such as the contour of the eyes, the contour of the lips and the region of the nasolabial folds. For example, the cosmetic composition may be applied uniformly over the whole face or on a particular area of the face.

A cosmetic composition according to the invention may be typically applied from 1 to 2 times a day, preferably morning and evening.

The application of the cosmetic is carried out at least for 7 days, preferably for at least 28 days, or even for several months.

As described hereafter, the cosmetic composition may be in any form suitable for application on the skin, in particular as a cream, a balsam, or a gel.

The cosmetic composition may comprise from 0.001% to 0.1% by weight, for example 0.015% to 0.040% by weight of swertiamarin.

The cosmetic method according to the invention may further comprise a maintenance phase which follows a first so called attack phase. The maintenance phase is characterized by the use of a cosmetic composition comprising a lower swertiamarin content or by a lower administration frequency of the cosmetic composition.

For example, for a method in which the cosmetic composition according to the invention may be applied twice a day in the attack phase, the number of applications may be reduced to once a day in the maintenance phase.

If necessary, the attack phase and the maintenance phase are characterized by the same daily frequency of application, but the cosmetic composition of the maintenance phase comprises a weight content of swertiamarin less by at least a factor 1.5, for example at least by a factor 2, 3, 4, 5, 6, 8, or 10, to the swertiamarin content of the cosmetic composition used in the attack phase.

The compositions adapted for the application of the uses and of the cosmetic or therapeutic processes according to the invention are detailed hereafter.

Compositions Containing Swertiamarin According to the Invention

The compositions adapted for applying the uses and the cosmetic or therapeutic processes according to the invention generally comprise from 0.0001% to 10% of swertiamarin and from 80% to 99.9999% of one or several pharmaceutically or cosmetically acceptable excipients.

As mentioned herein before, swertiamarin may be introduced into said composition in a purified or isolated form or in the form of a plant extract enriched with swertiamarin.

The pharmaceutically or cosmetically acceptable excipient(s) may be selected from diluents, dispersants, gelling agents, emollients, vectorization agents like polycationic polymer or phospholipids, gums, resins, solvents in particular lower alcohols especially ethanol, isopropanol, dipropylene glycol, butylene glycol, propanediol, glycerol, sorbitol, and propylene glycol, the fillers such as modified and polymerized starches, titanium dioxide, or a metal stearate, preservatives, essential oils, pearly agents, coloring agents, odor absorbers, pH regulating agents or neutralizers, lubricating agents, thickeners, surfactants including anionic, cationic, amphoteric or non-ionic surfactants, humectants, wetting agents, dispersants, aromatizing or perfuming agents, organic or further mineral pigments like iron oxides, oily agents like oils or fats of plant origin, fats of animal origin, synthetic oils like Vaseline, silicone oils (cyclomethicone), fatty acid esters (cetyl alcohol), fluorinated oils, waxes, modified clays, bentones, metal fatty acid salts, hydrophobicized silica, polyethylenes, mica, preservatives, antimicrobial agents, carriers such as a mineral, thermal or floral water, and/or other substances currently used in formulation in the cosmetic or pharmaceutical field.

In certain embodiments, swertiamarin is formulated by means of a vectorization system. By "vectorization system" is meant a supramolecular system, the purpose of which is to promote penetration of swertiamarin through the skin, preferably through the epidermis or even the dermis. In a preferred embodiment, swertiamarin is encapsulated in the vectorization system.

The vectorization system may be selected from the group consisting of micelles, liposomes, including unilamellar or multilamellar liposomes, niosomes, ethosomes, lamellar systems, nanosomes, lipid or polymeric vesicles, nanospheres, micro- or nano-particles of natural or non-natural polymers, hydrogels. Preferably, swertiamarin is encapsulated in a vectorization system selected from liposomes and lamellar systems. Particular examples of liposomes and of lamellar systems for the implementation of the present invention are inter alia described, in the French patent applications no. 1358589 and no. 1262303 filed in the name of the Applicant.

As an example, the vectorization system may be a lamellar system with lipid bilayers in an aqueous phase, said lamellar system comprising a mixture of phospholipid, fatty acid and fatty alcohol preferably having a "phospholipid/fatty acid" mass ratio from 0.5 to 1.5 and a "fatty alcohol/fatty acid" mass ratio from 2 to 4.

The fatty alcohol may be selected from the group consisting of capryl alcohol (octan-1-ol), capric alcohol (decan-1-ol), lauryl alcohol (dodecan-1-ol), myristyl alcohol (tetradecan-1-ol), palmitic alcohol (hexadecan-1-ol), stearyl alcohol (octadecan-1-ol), behenic alcohol (docosan-1-ol) and mixtures thereof.

The fatty acid may be selected from the group consisting of caprylic acid, capric acid, lauric acid, myristic acid, palmitic acid, stearic acid, behenic acid and mixtures thereof.

The phospholipid may be selected from the group consisting of phosphatidylcholine, phosphatidylserine, phosphatidylethanolamine, phosphatidylglycerol, phosphatidic acid, phosphatidylinositol, lysophospholipids, their hydrogenated derivatives and mixtures thereof.

As an additional example, the vectorization system may be a liposome comprising at least one phospholipid and at least one glycolipid preferably according to a "phospholipid/glycolipid" mass ratio ranging from 0.5 to 30, preferably from 1 to 10.

Preferably, the glucidic unit of the glycolipid comprises an oligomer or a polymer of fructose (fructan) such as a inulin or levan radical. The glycolipid is selected from stearoyl inulin, inulin lauryl carbamate, palmitoyl inulin, undecylenoyl inulin and mixtures thereof.

The phospholipid may be as defined earlier for the lamellar system.

The composition according to the invention may be in any known form. Preferably, this is a composition having a form adapted to topical administration. It may appear as aqueous, hydroalcoholic solutions, of oil-in-water emulsions (O/W) or water-in-oil (W/O) emulsions or multiple emulsions (triple: W/O/W or O/W/O), nanoemulsions, in particular O/W nanoemulsions, for which the drop size is less than 100 nm, aqueous gels, or dispersions of a fatty phase in an aqueous phase by means of spherules, of suspensions, preferably in an aqueous or hydroalcoholic media or further of a powder.

The composition according to the invention may appear as a lotion, a milk, a cream, an ointment, a gel, a foam, a solution, a pomade. The composition may also be included in a more complex system, for example within a bandage, or a patch, or an impregnated tissue, or appear as a tablet or a mucoadhesive film.

Preferably, the composition according to the invention is a pharmaceutical or cosmetic composition, preferably a cosmetic composition and still more preferably a dermocosmetic composition.

Thus, the composition according to the invention may also appear as a cosmetic product of any type. This may be a cosmetic care product or a makeup product or a body hygiene product, for example a lotion, a milk, a serum, an aqueous or oily gel, an emulsion, a cream, a cream-gel, a body care water, a pomade, a balm, a foundation, a spray, an eye shadow, a stick, a lipstick, a gloss, a foam, a deodorizer, a nutritive face mask, a shower gel, and exfoliating or scrubbing product. As an illustration and not as a limitation, swertiamarin may be present as a healing agent or for regeneration of the epidermis in a repair cream for damaged hands or further in a balm for chapped lips. Swertiamarin may also be present as an anti-wrinkle or anti-ageing agent in a day cream intended for mature or old skins. As an additional example, swertiamarin may be present as an agent for smoothing and/or restructuring the lips in a lipstick, a gloss or a lip balm. Swertiamarin may also be present as an anti-wrinkle agent or a smoothing agent in a care product for the contour of the eyes or of the lips. Swertiamarin may also be present as an anti-redness agent in a day cream intended to make the surface micro-vessels less visible.

Alternatively, the composition according to the invention may appear as a medicament intended to be applied on the skin or on a mucosa, for example a gel or a cream.

The cosmetic or pharmaceutical compositions according to the invention may be prepared according to standard methods, well known to the person skilled in the art.

"Precursor" Composition According to the Invention

According to an additional aspect, the object of the invention is a composition intended to be incorporated into a cosmetic or pharmaceutical composition. This composition therefore corresponds to a "precursor" composition.

Preferably, this composition for the preparation of a cosmetic or pharmaceutical composition comprises:

from 0.1 to 20%, preferably from 0.5 to 10%, of swertiamarin, said swertiamarin being preferably integrated as a plant extract enriched according to the invention.

from 50% to 99.9% of a carrier, preferably selected from a filler, an aqueous solvent, an organic solvent, preferably a lower alcohol such as ethanol, propanediol, butylene glycol, glycerol or isopropanol, a lipophilic agent and mixtures thereof, and optionally, from 0.1 to 30% of a pharmaceutically or cosmetically acceptable additional excipient, preferably selected from a vectorization agent, an antioxidant agent, a preservative, a stabilizer, a thickener, an emulsifier, a hydrophilic or lipophilic gelling agent, a perfume, a mineral or organic oil, and combinations thereof.

the percentages being expressed by weight based on the total weight of the cosmetic composition.

As mentioned herein before, the plant extract is preferably an extract obtained from a species of *Swertia* and having a swertiamarin content of at least 90%, preferably at least 95% by weight.

As a filler, mention may be made of silica and its derivatives such as magnesium silicate, talc, a starch, a starch derivative such as maltodextrin and a mixture thereof.

As a lipophilic agent, mention may be made of fatty acids, fatty acid esters such as isopropyl palmitate, and/or fatty alcohols, preferably $C_{10}$-$C_{30}$ fatty alcohols.

As an emulsifier or vectorization agent, mention may be made of phospholipids such as phosphatidylcholine, phosphatidylserine, phosphatidylethanolamine, phosphatidylglycerol, phosphatidic acid, phosphatidylinositol, lysophospholipids, hydrogenated derivatives thereof, and mixtures thereof.

The composition may comprise an aqueous or hydroalcoholic phase obtained from a mineral water, a thermal water or a floral water such as camomile, mallow, cornflower or *hamamelis* water.

Antioxidant agents inter alia comprise tocopherol and derivatives thereof, tocoquinone, HMR (hydroxy methyl resinol), polyphenols, isoflavones, propyl gallate, butylated hydroxy anisol (BHA), butylated hydroxy toluene (BHT) and derivatives thereof, histidine hydrochloride or further an extract of *Epilobium augustifolium*.

As an example of preservative compounds or of antimicrobial agents, mention may be made of 2-bromo-2-nitropropane-1,3-diol, behentrimonium chloride, benzalkonium chloride, benzyl alcohol, butylparaben, cetrimonium chloride, chlorhexidine derivatives (digluconate, dihydrochloride), chlorphenesin, climbazole, diazolidinyl urea. DMDM hydantoin, ethylparaben, hexamidin diisethionate, imidazolidinyl urea, iodopropynyl butylcarbamate, isobutylparaben, isopropylparaben, isothiazolinone, linalol, methyl benzoate, methylchloroisothiazolinone, methyldibromoglutaronitrile, methylisothiazolinone, methylparaben, o-cymen-5-ol, phenoxyethanol, piroctone olamine, polyaminopropyl biguanide, propylparaben, quaternium-15, sodium metabisulfite, sodium methylparaben, sodium propylparaben, stearalkonium chloride, triclosan, zinc pyrithione, caprylyl glycol, glyceryl caprate and caprylate, organic acids and their salts, preferably sodium or potassium salts, for example sorbic acid and its salts, benzoic acid and its salts, salicylic acid and its salts, formic acid and its salts, dehydroacetic acid and its salts, levulinic acid and its salts, or further anisic acid (methoxybenzoic acid) and its salts.

The "precursor" composition according to the invention may appear in different forms.

This may be a solid composition, preferably as a powder, in which swertiamarin may be absorbed on a filler. Alternatively, the composition may appear as an aqueous solution, a hydroalcoholic solution or a reverse emulsion (water-in-oil emulsion).

In a preferred embodiment, the "precursor" composition according to the invention is selected from:
- a solid composition appearing in the form of a powder in which swertiamarin is absorbed on a filler, and
- a composition appearing in the form of a water-in-oil emulsion comprising a lipophilic agent preferably selected from fatty acids, fatty acid esters and/or fatty alcohols and an emulsifier or vectorization agent selected from phospholipids, hydrogenated derivatives thereof and mixtures thereof.

As an example, the filler may be a maltodextrin and/or silica. As an additional example, the lipophilic agent is isopropyl palmitate and/or the vectorization agent is a phospholipid or a mixture of phospholipids, optionally hydrogenated, for example a hydrogenated or non-hydrogenated lecithin.

As a specific example, the "precursor" composition according to the invention may be as a powder comprising:
- from 0.5% to 5% by weight of a plant extract preferably of *Swertia* such as *Swertia Chirata*, enriched with swertiamarin,
- from 90% to 99.5% by weight of maltodextrin, the plant extract being absorbed on maltodextrin.

As an additional example, the "precursor" composition according to the invention may be a water-in-oil emulsion comprising:
- from 70% to 90% by weight of isopropyl palmitate,
- from 5% to 20% by weight of phospholipids, for example lecithin
- from 0.5% to 5% by weight of a plant extract preferably of *Swertia* such as *Swertia Chirata*, enriched with swertiamarin, and
- from 1% to 8% by weight of water.

The object of the present invention is also the use of said "precursor" composition for preparing a cosmetic or pharmaceutical composition. It is obvious that said final cosmetic or pharmaceutical composition is particularly adapted for the implementation of the therapeutic or cosmetic uses according to the invention, and may have any of the features described herein before in the part entitled "Compositions containing swertiamarin according to the invention".

The "precursor" composition may be present in the final cosmetic or pharmaceutical composition in an amount from 0.001% to 50%, preferably from 0.01% to 10% by weight based on the total weight of the final cosmetic or pharmaceutical composition.

Typically, the cosmetic or pharmaceutical composition may be obtained by mixing a "precursor" composition according to the invention with one or several excipients or pharmaceutically or cosmetically acceptable carriers.

It is obvious that an object of the present invention is also a process for preparing a cosmetic or pharmaceutical composition comprising a step of mixing the "precursor" composition according to the invention with one or several excipients or pharmaceutically or cosmetically acceptable carriers.

Other Uses of Swertiamarin According to the Invention

An object of the invention is also uses in vitro of swertiamarin, in particular in the field of research or in the medical field. Swertiamarin may be used for promoting the growth of skin explants in vitro. Skin explants may be used as a graft or self-graft for treating a skin lesion, or further for research purposes, for example for evaluating active agents.

An object of the invention is also a process for cultivation in vitro of a skin explant comprising a step of treating the skin explant with swertiamarin. The swertiamarin may be typically added into a suitable culture medium for cultivation or maintaining a skin explant or be applied on the explant.

Other aspects and advantages of the present invention will become apparent upon reading the examples which follow, which should be considered as illustrative and by no means as limiting.

EXAMPLES

Example 1

Swertiamarin Stimulates the Production of the Keratinocyte Growth Factor (KGF) by Adipocytes The goal of this study was to quantify the keratinocyte growth factor (KGF) in the culture medium of human adipocytes cultivated with and without swertiamarin.

Procedure

A stock solution at 10% by weight of swertiamarin in DMSO was prepared. This solution was then diluted in the culture medium so as to obtain a final concentration of 0.0075% by weight of swertiamarin.

A culture of normal human adipocytes, obtained from adipocytes sampled by abdominal plastic surgery in a 34 year old woman, was incubated for 15 hours with the culture medium containing swertiamarin. As a negative control, a culture of adipocytes incubated for 15 hours with a culture medium without any swertiamarin but containing the same amount of DMSO was used.

At the end of the incubation, the amount of KGF was quantified in each culture medium by an ELISA test. The statistical significance of the differences between the "control" groups and the "test groups" was evaluated by variance analysis (One way Anova) followed by the Holm Sida test ($p*<0.05$).

Results

Statistical analysis of the results obtained for the different groups of experiments show a significant increase in the amount of KGF in the culture media of the incubated adipocytes in the presence of swertiamarin as compared with the control groups. An amount of 0.0075% by weight of swertiamarin induces an increase in the average amount of KGF in the culture medium of about 16.4%.

Example 2

Swertiamarin Stimulates Proliferation of Keratinocytes

Model 1: The so-Called "Scratch Assay" Test

The goal of this study was to evaluate the effect of swertiamarin on a monolayer culture model of human keratinocytes.

Procedure

Normal keratinocytes surgically sampled in a 45 year old woman were cultivated so as to obtain a monolayer culture of keratinocytes.

When confluence was attained, a lesion ("scratch") was carried out in each cell culture so as to locally remove an equivalent amount of keratinocytes.

Each culture of keratinocytes was then incubated at 37° C. in a humid atmosphere and in the presence of 5% of $CO_2$, in the presence of an adipocyte culture medium conditioned with swertiamarin (0.0025%; 0.005%; 0.0075% by weight), for 72 hours. The swertiamarin was introduced into the adipocyte culture medium by dilution of a stock solution at 10% in DMSO. The final amount of DMSO in the culture media is 0.15%. As a control, an incubated keratinocyte culture was used under the same conditions in the presence of a culture medium comprising normal human adipocytes in suspension free of swertiamarin but containing 0.15% of DMSO (DMSO Control experiment). For validation purposes, a culture of keratinocytes was incubated in the presence of the growth factor TGF-β (10 ng/ml) under the same conditions (TGF-β Control).

The surface corresponding to the "lesion" (i.e. to the area where the keratinocytes were removed) was measured before (t=0) and after incubation for each cell culture from photographs obtained by optical microscopy by using the software package Image J.

The results were expressed as a percentage of re-colonized surface relative to the surface observed at t=0.

The statistical significance of the differences obtained between the groups "DMSO Control" and the groups "TGF-β Controls" was evaluated by using the t-test (***: $p<0.001$). The statistical significance of the differences obtained between the "DMSO Control" groups and the "SWT" test groups was analyzed by variance analysis (One way Anova) followed by the Holm Sida test ($p*<0.05$).

Results

Figure 1:
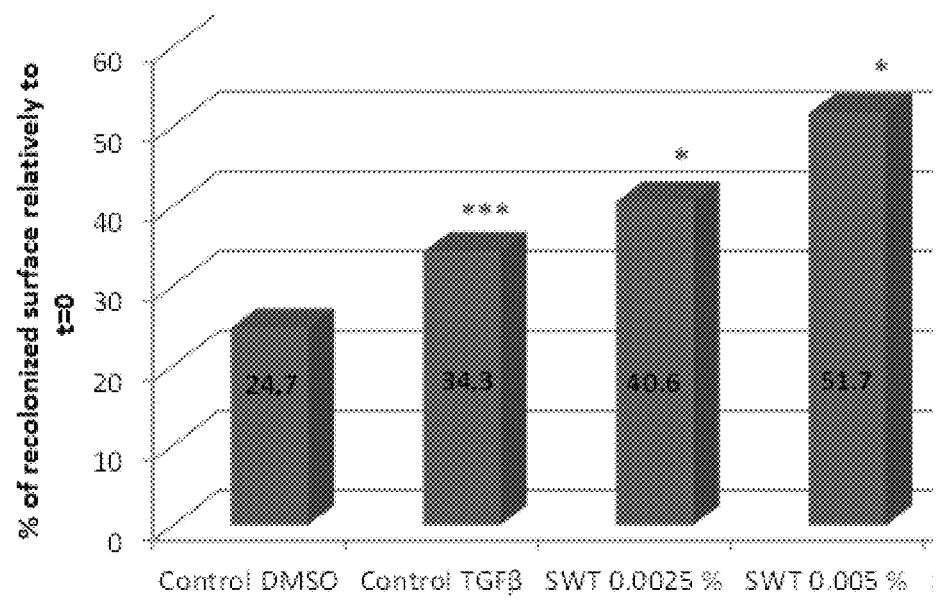
FIG. 1 shows the re-colonization percentage by keratinocytes in the so called "scratch test" (see Example 2) after incubation of adipocytes with swertiamarin (SWT) and conditioning of the keratinocyte medium with the adipocyte medium, with TGF-$\beta$ (reference product) or in the presence of only the dilution solvent (Control DMSO).

The obtained results are illustrated in FIG. 1 which shows the average re-colonization percentage obtained after incubation for each group of experiments.

Notably, the reference product, i.e. TGF-β, has significantly induced cell re-colonization after 72 hours of stimulation (+124.1%; $p<0.001$). This result was expected and allowed validation of the whole of the experiments.

Moreover, the adipocyte culture medium conditioned with swertiamarin stimulated significantly the proliferation of keratinocytes and re-colonization. Swertiamarin therefore strongly induced the healing process as compared with the "DMSO Control" experiments. This effect of inducting healing is observable at all the tested concentrations, including at 0.0025% of swertiamarin where an increase of +64.6% of the surface area re-colonized by the keratinocytes is observed as compared with the "DMSO Control" group.

Swertiamarin therefore stimulates the proliferation of keratinocytes and thus the regeneration of the epidermis.

Model 2: Skin Explant

The purpose of this study was to evaluate the effect of swertiamarin on human skin explants with and without adipose tissue.

Procedure

Skin samples were sampled surgically in a Caucasian woman during abdominal plastic surgery. 21 skin explants with a diameter of 10 mm were prepared from these samples, among which 12 are skin explants without any adipose tissue (epidermis+dermis explant) and 9 are full skin explants (epidermis+dermis+hypodermis). The explants are maintained alive in a BEM medium at 37° C. in the presence of a humid atmosphere with 5% of $CO_2$. The skin explants were distributed into three groups:

Group 1: a cream containing swertiamarin (SWT) in an amount of 0.025% was applied at days 0, 1, 2, 3, 6 and 7 of the incubation, to the surface of the skin explants by means of a spatula (1 μl in the morning and 1 μl in the evening), Group 2: a placebo cream (free of swertiamarin) was applied on days 0, 1, 2, 3, 6 and 7 of the incubation, to the surface of the skin explants by means of a spatula (1 μl in the mornings and 1 μl in the evenings), Group 3: this control group was maintained alive without any treatment (without application of a placebo cream or of cream based on swertiamarin).

On day 9, the skin explants are recovered, chemically bound in a formol solution for 24 hours, dehydrated, impregnated with paraffin and then infiltrated with resin according to the SOP H-53 protocol. Fine cuts are then made in each explant and observed by optical microscopy after staining.

Results

Figure 3:
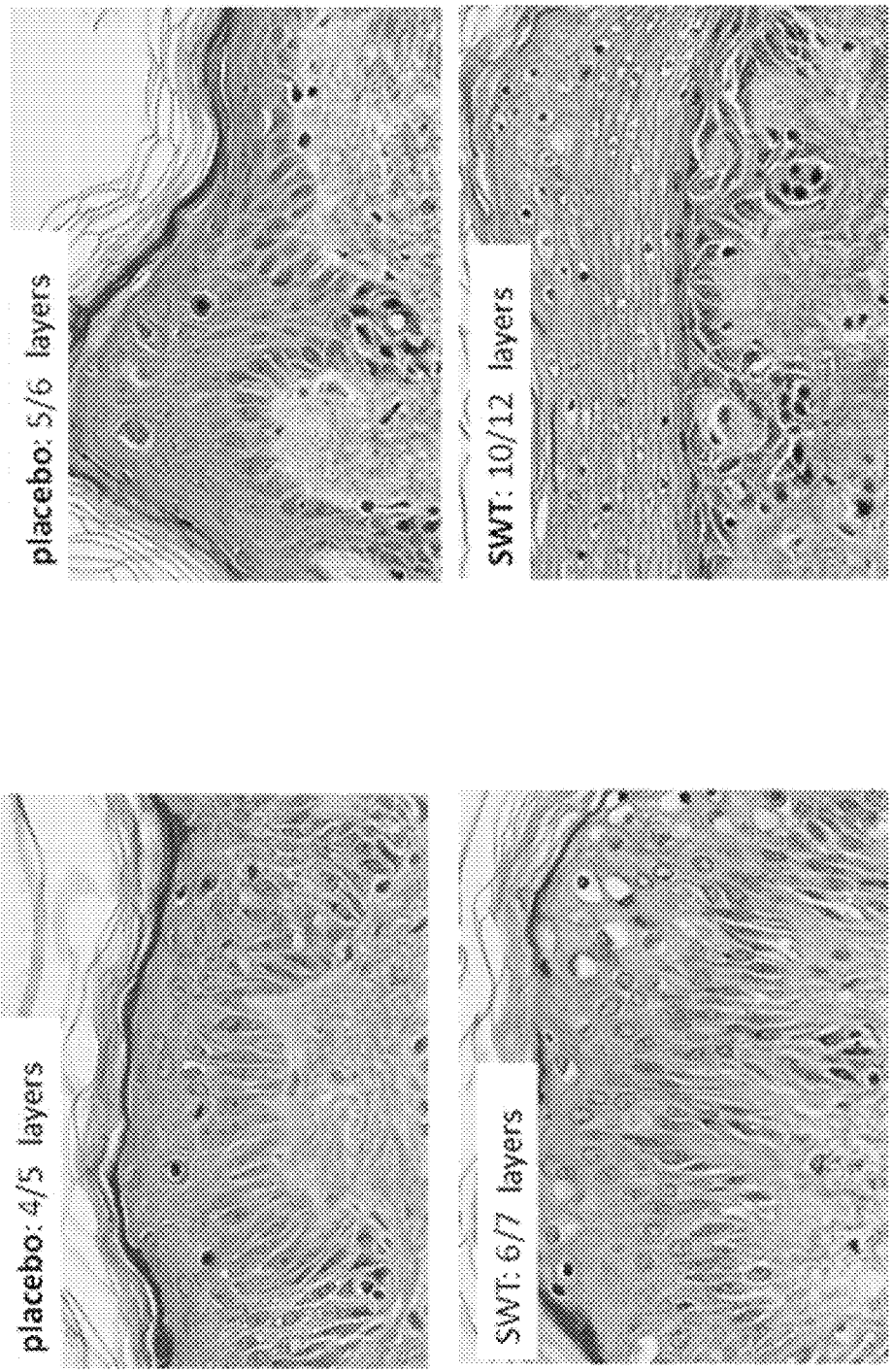
FIG. 3 shows skin explant sections with or without adipose tissue after incubation for 9 days with or without treatment with swertiamarin.

The full skin explants treated with swertiamarin have, after 9 days, between 10 and 12 cell layers of epidermis versus only 4-5 for the same untreated skin explants, and 4-5 for those treated with the placebo. The swertiamarin therefore has induced significant thickening of the epidermis. Further, the skin explants treated with swertiamarin do not exhibit any notable morphological alteration. The swertiamarin was also capable of inducing thickening of the epidermis in skin explants without any adipose tissue (thickness of 6 to 7 cell layers), which shows that swertiamarin also exerts a direct effect on keratinocytes. These results are illustrated in FIG. 3.

This experiment again illustrates the capability of swertiamarin to induce epidermis regeneration and keratinocytes proliferation.

Example 3

Swertiamarin Stimulates the Synthesis of Fibronectin by Fibroblasts of the Skin Fibronectin is an adhesion protein having a central role in the anchoring of the cells in the extracellular matrix. It is also involved in the modulation of cell functions. Fibronectin is essentially localized in the dermis and at the junction between the dermis and the epidermis. This protein is sensitive to proteolytic cleavage, a phenomenon which is enhanced during ageing and which has the consequence of affecting the entirety of the dermis by reducing the amount of fibronectin and by increasing the amount of denaturated proteins.

The goal of this study was to identify the effect of swertiamarin on the production of fibronectin by fibroblasts of this dermis.

Procedure

The applied test was based on the synthesis of fibronectin induced by TGF-β by cells of normal human fibroblasts of the dermis (NHDF) in a monolayer culture. The culture was produced by using as a culture medium DMEM (Eurobio, CMODME70-08) containing 10% of fetal calf serum (Eurobio, CVFSV00-0U), 1% of antibiotics (penicillin/streptomycin, Eurobio, CABPES01-OU) and 1% of L-glutamine (Eurobio, CSTGLUOO-OU), at a temperature of 37° C. under 5% of $CO_2$ and 95% of humidity.

The cells were then sown, in the presence of complete DMEM, in microplates in an amount of $2.5*10^4$ cells per well and then incubated at a temperature of 37° C. under 5% of $CO_2$ and 95% of humidity. The culture medium was replaced after 24 hours in order to bring the cells to a quiescent state.

Next, the cells were incubated in the presence of TGF-β or swertiamarin for 24 h or 48 h. The cell supernatants were then collected in order to quantify fibronectin by an ELISA test (BMS028, Ebiosciences). The cell viability level was also determined by the standard MTT test. As a control, cells were incubated under the same conditions but in the absence of TGF-β and of swertiamarin (control).

The results are expressed as a percentage of the amount of fibronectin produced per mL relative to the amount of fibronectin produced by the group of control experiments.

Results

Figure 2:
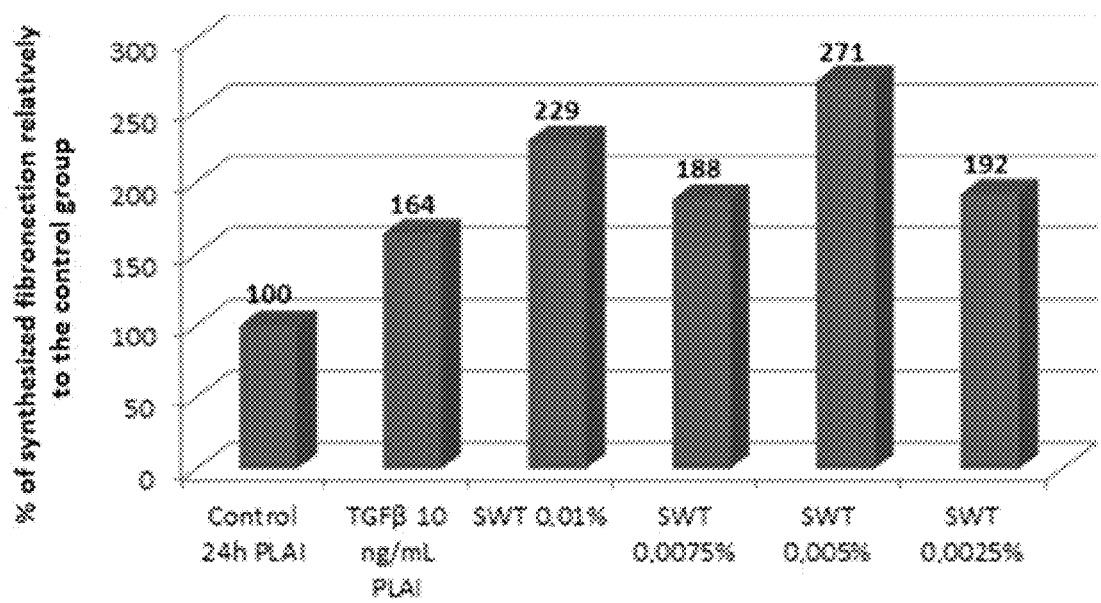
FIG. 2 shows the effect of swertiamarin and of TGF-$\beta$ on the synthesis of fibronectin by normal fibroblasts of the dermis relative to the control experiment (see Example 3).

The obtained results are illustrated in FIG. 2 which shows the average percentage of fibronectin produced in the experiment groups. The percentage is expressed with respect to the amount of fibronectin produced for the control experiment.

It is observed that the reference product, i.e. TGF-β, significantly induce the production of fibronectin (+64%). This result was expected and allowed validation of the whole of the experiments.

Remarkably, swertiamarin very strongly induced synthesis of fibronectin as compared with the control, and this at all the tested concentrations. This effect is generally greater than the one observed with TGF-β. As an illustration, a 0.005% concentration of swertiamarin induced and increased by more than 171% of the amount of fibronectin as compared with the control experiments.

Swertiamarin is therefore also capable of restoring or improving the integrity of the dermis by inducing synthesis of fibronectin.

Example 4

Examples of "Precursor" Compositions According to the Invention

The following precursor compositions were prepared from an extract of *Swertia Chirata* having at least 95% by weight content of swertiamarin (SWT extract hereafter).

Composition A (as a Powder):

| Composition A (% by weight) | |
| --- | --- |
| SWT extract | 1.25% |
| Silica | 2.00% |
| Maltodextrin | 96.75% |

Compositions B and C (Composition as a Hydroalcoholic Solution)

| Composition B (% by weight) | |
| --- | --- |
| SWT extract | 1.25% |
| Propanediol | 70.00% |
| Water | 28.75% |

| Composition C (% by weight) | |
| --- | --- |
| SWT extract | 1.25% |
| Glycerol | 70.00% |
| Water | 28.75% |

Composition D: Composition as a Reverse Emulsion

| Composition D (% by weight) | |
| --- | --- |
| Phospholipids | 15.8% |
| Isopropyl palmitate | 80.7% |
| Water | 2.25% |
| SWT extract | 1.25% |

Composition E: Composition as a Powder

| Composition E (% by weight) | |
| --- | --- |
| SWT extract | 1.25% |
| Maltodextrin | 98.75% |

Example 5

Examples of Cosmetic Compositions According to the Invention

As examples, the following cosmetic products may be prepared. These cosmetic products integrate one of the "precursor" compositions described herein before.

Anti-Stretch Marks Oily Gel

The swertiamarin extract is present therein as an agent for smoothing the skin. This oily gel may be applied on the skin to be treated, in particular on the breasts, on the abdomen and on the thighs, typically once to twice a day.

| Phase | Ingredient | INCI name | % by weight* |
|---|---|---|---|
| A | Emulmetik ™ 950 | Hydrogenated lecithin | 1.00 |
| B | Glycerol | Glycerol | 49.00 |
|   | Butylene Glycol | Butylene Glycol | 19.00 |
| C | Mirasil PTM | Phenyl trimethicone | 28.00 |
| D | Precursor composition D | Phospholipids (and) isopropylpalmitate (and) water (and) extract of *Swertia Chirata* | 2.00 |
| E | Sveltessence ™ | Glycerol (and) water (and) extract of seeds of *Nephelium Longana* | 1.00 |

*based on the total weight of the gel

Balm for Repairing Lips

The extract of swertiamarin is present therein as an agent for regenerating the epidermis for treating and preventing chapped skin. The lip balm may be applied on the lips typically once or twice a day.

| Phase | Ingredient (INCI designation) | % by weight* |
|---|---|---|
| A | *Euphorbia* wax | 9 |
|   | Microcrystalline cellulose | 4.40 |
|   | Ozokerite | 2.50 |
|   | Wax of *Copernicia cerifera* | 2.50 |
|   | Octyldodecanol | 10 |
|   | Cocoglycerides | 5.00 |
|   | Dicaprylyl carbonate | 4.00 |
|   | Propylheptylcaprylate | 6.00 |
|   | Polyglyceryl-2 triisostearate | 26.35 |
|   | Precursor composition D (SWT extract) | 2.50 |
| B | CI15850 | 1.80 |
|   | Ci77891 | 4.50 |
|   | Ci77499 | 0.15 |
|   | Lecithin (and) polyglyceryl-3-palmitate | 3.70 |
|   | Lecithin | 14.80 |
| C | Tocopherol (and) oil from seeds of *Helianthus annuus* | 0.50 |
|   | Perfume | 0.50 |
| D | Water (and) glycerol (and) extract of *Linum usitatissimum* seed | 1.30 |
|   | Water | 1.00 |
|   | Propanediol | 1.00 |
|   | Hydrogenated lecithin (and) $C_{12}$-$C_{16}$ alcohols (and) palmitic acid | 0.80 |
|   | Perfume | 0.20 |

*based on the total weight of the balm

Anti Wrinkle Day Cream

The extract of swertiamarin is present therein as an anti-wrinkle agent, i.e. as an agent for preventing or attenuating wrinkles and/or fine lines. This cream is typically applied on the face, preferably in the morning, on a clean skin and before application of makeup.

| Phase | Ingredient | INCI designation | % by weight* |
|---|---|---|---|
| A | Deionized water | water | 52.70 |
|   | FDC Red 4 Solution 0.1% | water (and) CI 14700 | 0.20 |
| B | Veegum HS | Magnesium and Aluminum Silicate | 0.50 |
|   | Glycerol | Glycerol | 5.00 |
|   | Natrosol 250 M Pharm | Hydroxyethylcellulose | 0.30 |

-continued

| Phase | Ingredient | INCI designation | % by weight* |
|---|---|---|---|
| C | Chlorphenesin | Chlorphenesin | 0.30 |
|   | Dermofeel ™ PA-3 | Sodium phytate (and) water | 0.10 |
|   | Biophilic ™ H | Hydrogenated lecithin (and) $C_{12}$-$C_{16}$ alcohols (and) palmitic acid | 4.00 |
| D | Cegesoft PS 6 | Plant oil | 3.00 |
|   | Cetiol C5 | Coco-Caprylate | 3.00 |
|   | Lipex Shea | Butter of *Butyrospermum Parkii* (Shea) | 5.00 |
|   | Dc 200, 5 Cs | Dimethicone | 3.50 |
|   | Dermofeel ™ BGC | Butylene Glycol Dicaprylate/Dicaprate | 7.00 |
|   | Dermofeel ™ GSC | Glyceryl Stearate Citrate | 1.00 |
|   | Stearin | Stearic acid | 1.00 |
|   | Dermofeel ™ Toco 70 Non Gmo | Tocopherol (and) oil from *Helianthus Annuus* seed | 0.20 |
| E | Lanablue ® | Sorbitol (and) water (and) algae extract | 1.00 |
|   | Mamaku Vital Essence Nature PF | Water (and) Glycerol (and) *Cyathea Medullaris* leaf extract | 2.00 |
|   | Sculptessence ™ | Water (and) Glycerol (and) extract of *Linum usitatissimum* seed | 5.00 |
|   | Precursor Composition C | Glycerol (and) water (and) extract of *Swertia Chirata* | 4.00 |
| F | Dermosoft ™ 1388 | Fragrance | 3.00 |
| G | SJ Touch 1 | Polymethyl Methacrylate | 2.00 |
| H | Elegance 4042 | Fragrance | 0.20 |

*based on the total weight of the cream

Anti-Redness Cream

| Phase | Ingredient | INCI designation | % by weight* |
|---|---|---|---|
| A | Deionized water | Water | 66.1 |
|   | Glycerol | Glycerol | 4 |
|   | Dermosoft ™ GMCY | Glyceryl Caprylate | 0.5 |
|   | Satiaxane CX 91 | Xanthan gum | 0.5 |
|   | Biophilic ™ H | Hydrogenated lecithin (and) $C_{12}$-$C_{16}$ alcohols (and) palmitic acid | 4 |
| B | Sunflower oil | *Helianthus Annuus* seed oil | 5 |
|   | Hazelnut oil | *Corylus Avellana* oil | 5 |
|   | Beeswax | Beeswax | 4 |
|   | Dermofeel ™ Toco 70 Non Gmo | Tocopherol (and) *Helianthus Annuus* seed oil | 0.2 |
|   | Shea Butter | *Butyrospermum Parkii* (Shea) Butter | 3 |
| C | Deionized Water | Water | 5 |
|   | Precursor composition A | Maltodextrin (and) silica (and) extract of *Swertia Chirata* | 2 |
| D | Potassium sorbate | Potassium sorbate | 0.3 |
| E | Relax 2020/2 | Fragrance | 0.4 |

*based on the total weight of the cream

Example 6

Swertiamarin Visibly Attenuates Face Wrinkles

The in vive effect of swertiamarin on face wrinkles was evaluated through 4 clinical tests.

The purpose of these tests was to demonstrate the effect of daily application of a cream containing 2% of composition D (i.e. about 0.024% of swertiamarin) on the depth of the wrinkles and the relief of the skin.

This cream, designated hereafter as "SWT cream", has the following composition:

| Phase | Ingredient | INCI designation | % by weight |
|---|---|---|---|
| A | Deionized water | Water | 69.95 |
|   | Dermofeel ™ PA3 | Sodium phytate (and) water (and) alcohol | 0.10 |
| B | Glycerol | Glycerol | 2.00 |
|   | Satiaxane CX911 | Xanthan gum | 0.25 |
| C | Heliofeel | Glyceryl Stearate Citrate (and) Polyglyceryl-3 Stearate (and) hydrogenated lecithin | 4.00 |
|   | Precursor composition D | Phospholipids and isopropyl palmitate and water and extract of *S. Chirata* | 2.00 |
|   | LIPEX ® 102 | *Butyrospermum Parkii* butter | 7.00 |
|   | Sweet Almond Oil | Sweet almond oil | 8.00 |
|   | Lanette ® 22 | Behenyl alcohol | 2.50 |
|   | Vitapherol E1000 | Tocopherol (and) *Helianthus annuus* seed oil | 0.20 |
| D | Dermosoft ™ 1388 | Perfume | 4.00 |
|   |   |   | 100.00 |

The cream "Placebo", used in the clinical tests, is distinguished from the "SWT" cream in that the extract of *S. chirata* in the precursor composition D was replaced with water.

The studies were interested in different types of facial wrinkles, in particular vertical wrinkles such as the goat wrinkle, the wrinkles of the region of the nasolabial folds and the wrinkles of the contour of the lips.

Vertical Wrinkles at the Bottom of the Face

The effect of swertiamarin on the vertical wrinkles of the bottom of the face was characterized by two clinical tests "swertiamarin vs. placebo".

Clinical Test No. 1:

The first clinical test had the purpose of evaluating the anti-wrinkle and smoothing effect of swertiamarin. 16 female volunteers, in good health, aged from 45 to 65 were enrolled. These volunteers received a "SWT cream" containing 2% of the composition D (i.e. about 0.024% of swertiamarin) and the "placebo cream" identical with the SWT cream but without any extract of *Swertia chirata*. Each volunteer applied on a first half of her face the "placebo cream" and on the second half of her face the "SWT cream", once in the morning and once in the evening for 28 days. The anti-wrinkle effect of swertiamarin was evaluated at the lower portions of the face at D=0, 7 and 28 of the treatment by means of the face imaging system Visia-CR® (Canfield Scientific) by using the "wrinkles" and "textures" filters. The analysis by imaging was focused on the wrinkles and the texture of the skin. The statistical processing of the data was carried out with a Student test on paired data (paired Student t-test). The treatment consisted of comparing the values obtained for the areas of the face treated with the SWT cream and the values obtained for the placebo cream, at different times (Dt) of treatment, by taking as a reference the values at D=0 (i.e. the pairs of data (D0, Dt) for the cream SWT were compared versus the pairs of data (D0, Dt) for the placebo cream).

Figure 4:
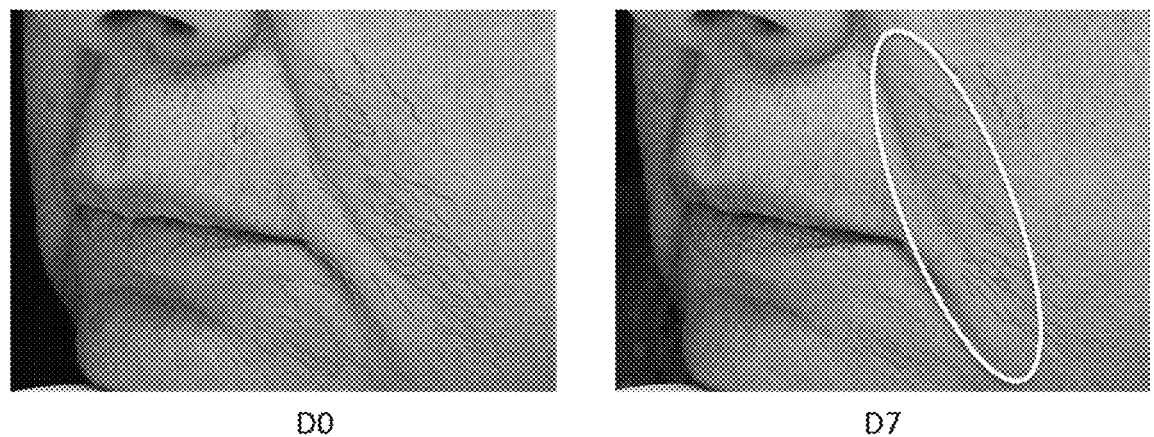
FIG. 4 shows the photographs of the low part of the face of a 51 year old volunteer at D=0 (D0) and after 7 days of treatment with the SWT cream (D7) at 0.024% of swertiamarin, morning and evening. On the photograph at D7 (D7), a clear decrease in the volume of the wrinkles and an attenuation of the nasolabial fold is noticed (see Example 6—clinical test no. 1).

The results of the study showed a significant reduction in the wrinkles (−16%, p<0.05) and of the roughness of the skin (−9%, p<0.05) after 28 days on the areas of the face treated with the "SWT" cream as compared with the areas of the face treated with the "placebo cream". Notably, the improvement in the aspect of the skin was ascertained as soon as the seventh treatment day. In certain individuals, a reduction of the wrinkles of 53% was able to be observed and a reduction of the roughness of the skin of 42% at D=7 as compared with D=0. As an example, FIG. 4 shows the photographs (with the "wrinkle" filter) of the low portion of the face of a volunteer of 51 years of age at D=0 (D0) and after 7 days of treatment with the SWT cream (D7). On the photograph at D7 (D7), a clear reduction of the surface area of the wrinkles at the cheek and a clear attenuation of the depth of the nasolabial fold are noted.

Clinical Test No. 2:

The purpose of this test was to confirm the anti-wrinkle and smoothing effect of swertiamarin on vertical wrinkles. 17 female volunteers in good health, aged between 45 and 65 years old, having vertical wrinkles in the lower portion of their face were enrolled for the needs of this study. The procedure followed was identical with that of clinical test no. 1. The anti-wrinkle effect was evaluated on days D=0, 7, 14 and 28 on the low portions of the face by a 3D analysis of the imprint of the skin in order to track the time-dependent evolution of the volume of the wrinkles over time by profilometry by projecting fringes (fringe projection) on the skin imprint. Statistical analysis was carried out with a Student-test on paired data.

The obtained results confirm the anti-wrinkle effect observed during the first clinical test: a clear reduction in the volume of vertical wrinkles for the areas of the face treated with the "SWT cream" was ascertained as soon as the $7^{th}$ day of treatment as compared with the areas of the face treated with the placebo cream. The application of the SWT cream gave the possibility of notably limiting the volume of the vertical wrinkles. This effect is illustrated with FIG. 5 which shows the percentage of variation of the volume of the wrinkles as compared with the reference value measured at D=0, for skins treated with the placebo cream (Placebo) and skins treated with the "SWT" cream. An increase in the volume of the wrinkles is observed for the skins treated with the placebo cream. On the other hand, twice daily application of the "SWT cream" gives the possibility of reducing the volume of the wrinkles over time, illustrating the anti-wrinkle effect of swertiamarin.

Wrinkles of the Contour of the Lips

Two additional clinical tests were carried out by a dermatologist in order to characterize the effect of swertiamarin on the wrinkles of the contour of the lips.

Clinical Test No. 3:

This test enrolled 10 volunteer women in good health, smokers, aged from 45 to 65 years old, having pronounced wrinkles at the lips (typical of regular consumption of tobacco). The volunteers received a "SWT cream" containing 2% of composition D (i.e. about 0.024% of swertiamarin) and a "placebo cream" with the instruction of applying a first cream on the first half of their face, and the second cream on the other half of their face, in the morning and in the evening, for 28 days. At the treatment days D=0, 7 and 28, an analysis of the change of the skin relief on each half of the face was conducted by using the Primos® 3D Pico system (based on the so called "Fringe projection" technique). This analysis was focussed on the wrinkles of the lips and had the purpose of determining the average roughness (Ra). Ra corresponds to the ratio between the integrated surface around the average value over the length of the profile. A reduction of Ra characterized a smoothing effect. The statistical analysis was carried out with Student's test on paired data (paired Student t-test).

The analysis of the change in the skin relief holds a significant reduction in the average roughness (Ra) (−19%, p<0.05) after 28 days on the area of the contour of the lips treated with "SWT cream" as compared with the areas treated with the "Placebo cream". As an example, FIG. 6 shows macrophotographs of the contour of the lips of a 64 year old volunteer at D=0 (D0), D=7 (D7) and D=28 (D28) of the treatment with the SWT cream. A clear reduction in the relief of the wrinkles is observed at the upper contour of the lip on the macrophotographs D7 and D28. The skin appears smoother.

Clinical Test No. 4:

This test enrolled 10 volunteer women in good health, smokers, aged from 45 to 65 years old having pronounced wrinkles at the lips. Each woman enrolled in the clinical test uniformly applied the "SWT" cream on the whole of her face, for 28 days, twice daily (morning and evening).

A lipstick migration test was conducted at D=0 and D=28 of the procedure. For this purpose, lipstick was applied on the whole of the lips of each volunteer at D=0 and D=28. Two hours after application of the lipstick, photographs of the lips were made with cross-polarized light and Prolite® flashes by using a still camera D7100 Nikon with a 60 mm Nikon lens. The shots were taken with an obstruction rate of $\frac{1}{125}^{th}$ second and a diaphragm on f22. The positioning of the individuals was standardized in order to observe the ⅓ proportion.

The photographs were viewed on a computer. The migration score was determined by the technician in charge of the study and an independent technician at D=0 and D=28 according to the following scale: 0: no migration, 1: slight migration, 2: moderate migration, 3: significant migration, 4: very significant migration.

This clinical test gave the possibility of observing migration of the lipstick, on average twice less significant at D=28 than at D=0 on the whole of the enrolled women.

In certain women, application of the SWT cream twice daily, for 28 days, gave the possibility of reducing by a factor 7 the migration score of the lipstick as compared with the migration data determined at D=0.

As an example, FIG. 6 shows the photograph of the contour of the lips of a 50 year old volunteer at D=0 (D0), and at D=28 (D28) of the treatment with the SWT cream. The migration of the lipstick is significantly more significant at D=0 than at D=28.

The results of this study emphasize once more, the capability of swertiamarin of attenuating wrinkles.

The invention claimed is:

1. A method for treating wrinkles and/or skin fine lines in a woman at least 45 years old comprising topically administering to said woman a cosmetic composition comprising a swertiamarin-enriched extract from a *Swertia* species to a portion of the skin showing wrinkles and/or fine lines, wherein:
the swertiamarin-enriched extract is added to the cosmetic composition as a water-in-oil emulsion comprising from 70% to 90% by weight of isopropyl palmitate, from 5% to 20% by weight of phospholipids, from 0.5% to 5% by weight of said swertiamarin-enriched extract, and from 1% to 8% by weight of water,
swertiamarin represents from 0.01% to 0.1% by weight of the total weight of said cosmetic composition and
the treated portion of skin is selected from the neck, the hands, the contour of eyes, the contour of lips, the nasolabial folds and combinations thereof and exhibits an increase or restoration of the thickness of the epidermis and exhibits reduced wrinkles and fine lines.

2. The method of claim 1, wherein the cosmetic composition comprising the swertiamarin-enriched plant extract is administered to the woman to stimulate metabolism of dermis in said woman.

3. The method of claim 1, wherein the swertiamarin-enriched plant extract is obtained from a species of *Swertia* and comprises at least 90% by weight of swertiamarin.

4. The method of claim 1, wherein swertiamarin represents from 0.015% to 0.04% by weight of the total weight of said cosmetic composition.

5. The method of claim 1, wherein said cosmetic composition further comprises at least one additional cosmetic active agent selected from the group consisting of vitamins, sun filters and sunscreens, anti-aging agents, anti-wrinkle agents, antioxidants, lifting agents, firming agents, anti-spot agents, anti-redness agents, thinning agents, draining agents, moisturizers, soothing agents, scrubbing agents, exfoliating agents, mattifying agents, sebum regulating agents, skin-lightening actives, self-tanning actives, tanning accelerators and combinations thereof.

6. The method of claim 1, wherein the cosmetic composition is selected from the group consisting of aqueous solutions, hydro-alcoholic solutions, oil-in-water emulsions (O/W), water-in-oil emulsions (W/O), multiple emulsions, nanoemulsions for which the size of the drops is less than 100 nm, aqueous gels, and dispersions of a fatty phase in an aqueous phase by means of spherules, suspensions, suspensions of liposomes, powders, lotions, milks, creams, ointments, gels, foams, and pomades.

7. The method of claim 1, wherein the cosmetic composition is applied from 1 to 2 times a day to the woman.

8. A method for treating wrinkles and/or skin fine lines in a woman at least 45 years old comprising topically administering to said woman a cosmetic composition comprising a swertiamarin-enriched extract from a *Swertia* species to a portion of the skin showing wrinkles and/or fine lines, wherein
the swertiamarin-enriched extract is added to the cosmetic composition as a powder comprising from 0.5% to 5% by weight of the swertiamarin-enriched extract, and from 90% to 99.5% by weight of maltodextrin, the swertiamarin-enriched extract being absorbed on maltodextrin,
swertiamarin represents from 0.01% to 0.1% by weight of the total weight of said cosmetic composition and
the treated portion of skin is selected from the neck, the hands, the contour of eyes, the contour of lips, the nasolabial folds and combinations thereof and exhibits an increase or restoration of the thickness of the epidermis and exhibits reduced wrinkles and fine lines.

9. The method of claim 8, wherein the cosmetic composition comprising the swertiamarin-enriched plant extract is administered to the woman to stimulate metabolism of dermis in said woman.

10. The method of claim 8, wherein the swertiamarin-enriched plant extract is obtained from a species of *Swertia* and comprises at least 90% by weight of swertiamarin.

11. The method of claim 8, wherein the swertiamarin represents from 0.015% to 0.04% by weight of the total weight of said cosmetic composition.

12. The method of claim 8, wherein said cosmetic composition further comprises at least one additional cosmetic active agent selected from the group consisting of vitamins, sun filters and sunscreens, anti-aging agents, anti-wrinkle agents, antioxidants, lifting agents, firming agents, anti-spot agents, anti-redness agents, thinning agents, draining agents, moisturizers, soothing agents, scrubbing agents, exfoliating agents, mattifying agents, sebum regulating agents, skin-lightening actives, self-tanning actives, tanning accelerators and combinations thereof.

13. The method of claim 8, wherein the cosmetic composition is selected from the group consisting of aqueous solutions, hydro-alcoholic solutions, oil-in-water emulsions (O/W), water-in-oil emulsions (W/O), multiple emulsions, nanoemulsions for which the size of the drops is less than 100 nm, aqueous gels, and dispersions of a fatty phase in an aqueous phase by means of spherules, suspensions, suspensions of liposomes, powders, lotions, milks, creams, ointments, gels, foams, and pomades.

14. The method of claim 8, wherein the cosmetic composition is applied from 1 to 2 times a day to the woman.

\* \* \* \* \*